(12) United States Patent
Bruns et al.

(10) Patent No.: US 8,563,767 B2
(45) Date of Patent: Oct. 22, 2013

(54) METHOD FOR PRODUCING ISOCYANATES IN THE GAS PHASE

(75) Inventors: Rainer Bruns, Leverkusen (DE); Wolfgang Lorenz, Dormagen (DE); Knut Sommer, Krefeld (DE)

(73) Assignee: Bayer MaterialScience AG, Leverkusen (DE)

( * ) Notice: Subject to any disclaimer, the term of this patent is extended or adjusted under 35 U.S.C. 154(b) by 80 days.

(21) Appl. No.: 13/382,609

(22) PCT Filed: Jun. 26, 2010

(86) PCT No.: PCT/EP2010/003915
§ 371 (c)(1),
(2), (4) Date: Feb. 6, 2012

(87) PCT Pub. No.: WO2011/003531
PCT Pub. Date: Jan. 13, 2011

(65) Prior Publication Data
US 2012/0302785 A1    Nov. 29, 2012

(30) Foreign Application Priority Data
Jul. 9, 2009  (DE) .......................... 10 2009 032 414

(51) Int. Cl.
*C07C 263/10*    (2006.01)

(52) U.S. Cl.
USPC ......................................................... 560/347

(58) Field of Classification Search
USPC ......................................................... 560/347
See application file for complete search history.

(56) References Cited

U.S. PATENT DOCUMENTS

| | | |
|---|---|---|
| 4,847,408 A | 7/1989 | Frosch et al. |
| 5,449,818 A | 9/1995 | Biskup et al. |
| 5,679,839 A | 10/1997 | Armand et al. |
| 6,803,482 B2 | 10/2004 | Jenne et al. |
| 7,541,487 B2 | 6/2009 | Pohl et al. |
| 2009/0221846 A1 | 9/2009 | Wölfert et al. |

OTHER PUBLICATIONS

Hartung, K.H. et al, Beschleunigung der turbulenten Mischung in Rohren, Chemie-ing.-Techn. 44 (1972), p. 1055, Fig. 10.

*Primary Examiner* — Brian J Davis
(74) *Attorney, Agent, or Firm* — Robert S. Klemz; Lyndanne M. Whalen

(57) ABSTRACT

An isocyanate is produced by continuously reacting an amine with phosgene in the presence of an inert substance in the gas phase. In this process, a phosgene-containing stream and a stream containing both the amine and the inert substance are fed into a reactor. The molar ratio of the inert substance to the amino groups in the stream is greater than 0 but less than 45 mol %. This molar ratio changes by no more than 99% during a 20 minute period.

8 Claims, No Drawings

METHOD FOR PRODUCING ISOCYANATES IN THE GAS PHASE

The invention relates to a process for the continuous preparation of isocyanates by reaction of the corresponding amines with phosgene in a reactor in the gas phase in the presence of at least one inert substance, wherein a phosgene-containing stream and a stream containing the amine and the inert substance are fed to the reactor, and wherein the molar ratio of the inert substance to the amino groups in the stream is not subject to wide variations.

Isocyanates are prepared in large amounts and serve chiefly as starting substances for the preparation of polyurethanes. They are usually prepared by reaction of the corresponding amines with phosgene. One possibility of the preparation of isocyanates is the reaction of the amines with the phosgene in the gas phase. This process procedure, which is conventionally called gas phase phosgenation, is distinguished in that the reaction conditions are chosen such that at least the reaction components amine, isocyanate and phosgene, but preferably all the educts, auxiliary substances, products and reaction intermediate products, are gaseous under the conditions chosen. Advantages of gas phase phosgenation are, inter alia, a reduced phosgene hold-up, the avoidance of intermediate products which are difficult to phosgenate and increased reaction yields. The present invention relates exclusively to gas phase phosgenation.

Various processes for the preparation of isocyanates by reaction of amines with phosgene in the gas phase are known from the prior art.

EP-A-289 840 describes the preparation of diisocyanates by gas phase phosgenation, wherein the preparation takes place in a turbulent flow at temperatures of between 200° C. and 600° C. in a cylindrical space without moving parts. According to the teaching of EP-A-289 840, for it to be possible to carry out the process disclosed in EP-A-289 840 it is essential for the dimensions of the tube reactor and the flow rates in the reaction space to be such that a turbulent flow which, according to the teaching of EP-A-289 840, is characterized by a Reynolds number of at least 2,500 prevails in the reaction space. According to the teaching of EP-A-289 840, this turbulence is in general ensured if the gaseous reaction partners pass through the reaction space with a flow rate of more than 90 m/s. Due to the turbulent flow in the cylindrical space (tube), disregarding fluid elements close to the wall, a relative good flow equipartition in the tube and therefore a relatively narrow dwell time distribution is achieved, which, as described in EP-A-570 799 (see below), leads to a reduction in the formation of solids. The use of amines in dilute form is furthermore disclosed, inert gases (preferably nitrogen) or vapours of inert solvents (such as chlorobenzene, dichlorobenzene, xylene, chloronaphthalene or decahydronaphthalene) being described as diluents. The specification states that a dilution can be effected adhering to a volume ratio of diamine vapour to inert gas or solvent vapour of from 1:0.5 to 1:2. Nevertheless, the specification expressly denies that the amount of diluents employed could play a critical role (p. 3, column 3, l. 46-48).

EP-A-570 799 relates to a process for the preparation of aromatic diisocyanates, characterized in that the reaction of the associated diamine with the phosgene is carried out in a tube reactor above the boiling temperature of the diamine within an average contact time of from 0.5 to 5 seconds, As described in the specification, both reaction times which are too long and those which are too short lead to an undesirable formation of solids. A process is therefore disclosed in which the average deviation from the average contact time is less than 6%. Adherence to this contact time is achieved by carrying out the reaction in a tubular flow which is characterized either by a Reynolds number of above 4,000 or by a Bodenstein number of above 100. If the tubular flow is characterized, by a Reynolds number above 4,000, it is also a disadvantage here that because of the necessary high flow rates, realization, of the dwell time necessary for complete reaction of the amines is possible only in very long mixing and reactor tubes. The possibility of dilution of the amine is furthermore disclosed, the same diluents as in EP-A-289 840 being described. Only a typical volume ratio of diluent to diamine in the range of from 1:0.5 to 1:2 is described. The consequences adverse ratios of diluent to amine can have is not the subject matter of the teaching of EP-A-570 799. According to the teaching of EP-A-570 799, even small deviations from the average contact time lead to an undesirable formation of solids and a shortened service life of the reactor.

EP-A-699 657 describes a process for the preparation of aromatic diisocyanates in the gas phase, characterized in that the reaction of the associated diamine with the phosgene takes place in a reactor comprising two zones, wherein the first zone, which makes up about 20% to 80% of the total reactor volume, is mixed ideally and the second zone, which makes up 80% to 20% of the total reactor volume, can be characterized by a piston flow. The second reaction zone is preferably configured as a tube reactor. However, because at least 20% of the reaction volume is back-mixed in an ideal manner, a non-uniform dwell time distribution results, which can lead to an undesirable increased formation. of solids, The use of the amine in concentrations of from 3 to 30% in a diluent is furthermore disclosed (in Example 2 ortho-dichlorobenzene). The consequences adverse ratios of diluent to amine can have is not the subject matter of the teaching of EP-B-699 657.

Optimization of the use of tube reactors for gas phase phosgenation as disclosed fundamentally in EP-A-570 799 using the jet mixer principle (*Chemie-Ing.-Techn.* 44 (1972) p. 1055, FIG. 10) is the subject matter of numerous applications.

According to the teaching of EP-A-1 362 847, equalizing of the educt stream fed via the annular space of the tube reactor and feeding of the two educt streams as centrally as possible into the tube reactor has a great positive influence on the stability of the reaction zone and therefore on the gas phase reaction overall. As a consequence of the more stable reaction procedure, the temperature variations observed decrease significantly and the asymmetry in the temperature distribution to be observed without the measures disclosed disappears practically completely. According to the teaching of EP-A-1 362 847, temperature variations and asymmetries in the temperature distribution lead to the formation of by-products, which lead to caking and blockages in the reactor and therefore to a shortening of the service life of the reactors. However, specific indications for conversion of the process disclosed into an industrial scale are not disclosed in EP-A-1 362 847. The optional use of a diluent (inert gases or vapours of inert solvents) is furthermore disclosed, the application not going into details with respect to the amounts of streams and ratios of amounts to be adhered to.

A further development of the use of tube reactors for gas phase phosgenation as disclosed fundamentally in EP-A-570 799 using the jet mixer principle (*Chemie-Ing.-Techn.* 44 (1972) p. 1055, FIG. 10) is the subject matter of WO2007/028715. WO2007/028715 discloses a process for the preparation of isocyanates by phosgenation of the corresponding amines in the gas phase in a reactor, characterized in that the reactor employed has a mixing device and a reaction space.

According to the teaching of WO2007/028715, the reaction space includes in the front region the mixing space in which mixing of the gaseous educts phosgene and amine, optionally mixed with an inert medium, predominantly takes place, which as a rule is accompanied by the start of the reaction. According to the teaching of WO2007/028715, essentially only the reaction and at most to a minor extent the mixing then takes place in the rear part of the reaction space. Preferably, in the process disclosed in WO2007/028715 reaction spaces which are rotationally symmetric to the direction of flow and can be broken down in construction terms essentially into up to four longitudinal sections along the longitudinal axis of the reactor in the course of flow are employed, the longitudinal sections differing in the size of the flowed-through cross-sectional area. A disadvantage of the process disclosed is the high flow rate of from preferably 10 to 300 m/s, particularly preferably 40 to 230 m/s, very particularly preferably 50 to 200 m/s, in particular more than 150 to 190 m/s and specifically 160 to 180 m/s, with which the gaseous reaction mixture passes through the reaction space. As already described in EP-A-570 799, because of the high flow rates, realization of the dwell time necessary for complete reaction of the amines, especially if aromatic primary amines are employed, is possible only in very long reactor tubes. A disadvantage is likewise that the changes in the flowed-through cross-sectional area of the reaction space are generated by a volume body in a tube reactor, and the conversion of the reactor construction disclosed into an industrial scale is therefore expensive in construction terms. With respect to the optional use of an inert medium, the application discloses that the ratio of the gas volumes of inert medium to amine or to phosgene is more than 0.0001 to 30, preferably more than 0.01 to 15, particularly preferably more than 0.1 to 5. The influence adverse ratios of inert medium to amine or phosgene can have is not the subject miter of the teaching of WO2007/028715.

EP-A-1 935 876 describes the advantages of an adiabatic reaction procedure, which lie in avoidance of temperature control problems and relatively high space/time yields. Here also, the optional use of an inert medium (inert gases or vapours of inert solvents) during vaporization of the amine is disclosed, the application not going into details with respect to the amounts of streams and ratios of amounts to be adhered to. The specification teaches that if a minimum dwell time once determined for the complete reaction for the particular system based on the start temperature, adiabatic increase in temperature, molar ratio of the reactants, dilution gas and amine employed is exceeded by less than 20%, preferably by less than 10%, the formation of secondary reaction products can be largely avoided.

The use of inert substances for dilution of the educts amine and/or phosgene is thus prior art. In particular, dilution of the amine is general practice. The reason for this is that suitable inert substances, often nitrogen, act as entraining agents and facilitate vaporization of the amine, as a result of which decomposition reactions (for example with splitting off of ammonia) are reduced. Thus, for example, the addition of even small amounts of nitrogen to toluylenediamine (as a rule a mixture of various isomers, summarized by the abbreviation TDA in the following) has the effect of significantly reducing the vaporization temperature. For example, the addition of 4 wt. % of nitrogen leads to a reduction in the vaporization temperature of TDA by approx. 8° C. Small amounts of an inert gas are thus already sufficient to lower the vaporization temperature.

With this procedure it is important that the ratio of inert substances to amine to be vaporized is not subjected to wide variations. For example, in the case of phosgenation of TDA using nitrogen to facilitate vaporization of the TDA, if the stream of nitrogen drops suddenly as a result of a malfunction, this leads to a sudden increase in the vaporization temperature of the TDA and to a brief drop in the amount of TDA vaporized. The instability of the TDA gas stream to the reactor resulting from this has disastrous consequences as a result of the high rate of the gas phase phosgenation. Due to the reduction in the TDA stream, the stream of hydrogen chloride gas liberated, as a product coupled with the reaction, is also very significantly reduced briefly, since on the basis of the stoichiometry of the reaction 4 times the amount of HCl gas, based on TDA, is liberated, which in turn, together with the reduced amount of nitrogen, leads to a significant drop in pressure in the reactor. The molar ratio of the reactants furthermore changes, and as a result of this the adiabatic jump in temperature in an adiabatic reaction procedure. The small deviation from the average contact time of only 6% required according to the teaching of EP-A-570 799 is not adhered to.

A briefly increased stream of nitrogen likewise has dramatic effects on the reaction. In this case, briefly more TDA vaporizes, and the amount of hydrogen chloride gas liberated, as a product coupled with the reaction, briefly increases sharply, which leads to a brief increase in the reaction pressure. In this case also, the molar ratio of the reactants is disturbed, with effects on the adiabatic temperature jump of the reaction, and furthermore the small deviation from the average contact time of only 6% required in EP-A-570 799 is not adhered to.

Both a decreasing and an increasing stream of nitrogen thus lead to disturbances in the gas phase phosgenation reaction, and in particular by disturbing the stoichiometry sought for the reactants, Which according to the teaching from the prior art leads to increased formation of by-products and formation of a solid deposit, which can considerably impair the reaction and in the worst case can make it necessary to shut down the reactor. The minimum dwell time initially determined for the system is not adhered to, which according to the teaching from the prior art leads to the formation of secondary products of the reaction. Because of the speed of the gas phase phosgenation, the flash temperature of the reaction changes very quickly and variations in temperature occur, which according to the teaching according to the prior art leads to the formation of by-products, which lead to caking and blockages in the reactor and therefore to a shortening of the service life of the reactors.

When carrying out the process in practice, a ratio between the inert substances and the educt which is not stable over time can consequently lead to a deviation from the average contact time with the adverse consequences from the prior art for the gas phase reaction procedure. None of the specifications disclosed to date is concerned with these problems, and a solution to them is therefore not to be deduced from the prior art.

The object of the present invention was therefore to provide a process for the gas phase phosgenation of amines which utilizes the advantages of dilution of the amine with inert substances without the problems described above impairing the progress of the operation.

It has been found that the object can be achieved by a process for the continuous preparation of isocyanates by reaction of the corresponding amines with phosgene in a reactor in the gas phase in the presence of at least one inert substance, characterized in that a phosgene-containing stream and a stream containing the amine and the inert substance are fed to the reaction, wherein the molar ratio of the inert substance to the amino groups in the stream (i) is always>0 and<45 mol %, preferably between 0.05 and 25 mol %, particularly preferably between 0.1 and 10 mol %, and (ii) within a period of 20 minutes changes by a maximum of 99%, preferably not more than 80%, particularly preferably not more than 60%, based on the time at the start of the period of 20 min.

If the stream containing the amine and the inert substance contains two or more inert substances, the molar ratio in (i) and in (ii) is calculated with the sum of the moles of the inert substances.

Primary amines are preferably employed here. Preferably, primary aromatic amines which can be converted into the gas phase essentially without decomposition are employed. Primary aromatic diamines are preferred in particular.

Examples of preferred aromatic amines are toluylenediamine (TDA), in particular 2,4-TDA and 2,6-TDA and mixtures thereof, diaminobenzene, naphthyldiamine (NDA) and 2,2'-, 2,4'- or 4,4'-methylenediphenyldiamine (MDA) or isomer mixtures thereof Toluylenediamine (TDA), in particular 2,4-TDA and 2,6-TDA and mixtures thereof, is particularly preferred.

Primary amines, in particular primary diamines, based on aliphatic or cycloaliphatic hydrocarbons having 2 to 18 carbon atoms are furthermore particularly suitable, Very particularly suitable amines are 1,6-diaminohexane, 1-amino-3,3,5-trimethyl-5-aminomethylcyclohexane (IPDA) and 4,4'-diaminodicyclohexylamine.

An inert substance in the context of the inventions is a substance which is present in the reaction space in gaseous form at the reaction temperature and does not substantially react with the compounds occurring in the course of the reaction. This means that less than 10 mol %, preferably less than 5 mol %, particularly preferably less than 3 mol % and very particularly preferably less than 1 mol % of the inert substance reacts chemically under the reaction conditions. An inert substance in the context of the invention exceptionally particularly preferably does not react chemically at all under the reaction conditions. Possible inert substances are, for example, on the one hand those substances which are already gaseous at room temperature, that is to say, for example, nitrogen, noble gases such as helium or argon, and other gases such as carbon dioxide or carbon monoxide. On the other hand, possible inert substances are also those which are gaseous only at temperatures above room temperature, that is to say, for example, aromatics such as chlorobenzene, chlorotoluene (o-, m-, p-isomers), dichlorobenzene (o-, m-, p-isomers), toluene, xylene (o-, m.-, p-isomers), chloronaphthalene (all isomers) or decahydronaphthalene. In the group of substances which are already gaseous at room temperature, nitrogen is particularly preferred, because this meets the criteria with respect to chemical inertness extremely well and is considerably cheaper than noble gases here (which would result in effects of a similar order of magnitude and have an even lower chemical reactivity). In the group of substances which are gaseous only above room temperature, substances which are also used as a solvent in the process are preferred. Chlorobenzene and dichlorobenzene are particularly preferred. The inert substances in the context of the present invention can furthermore be characterized according to their whereabouts in the gas phase process. Substances which are already gaseous at room temperature, such as, for example, nitrogen, noble gases such as helium or argon, and other gases such as carbon dioxide or carbon monoxide, are essentially sluiced out of the process in gaseous form with hydrogen chloride, the gaseous product formed which is coupled with the reaction, and must therefore constantly be freshly fed in.

Substances which are gaseous only above room temperature, on the other hand, are not sluiced out in gaseous form with hydrogen chloride, the gaseous product coupled with the reaction, but remain in the process and can be used again, where appropriate after purification by distillation, as the inert substance for dilution of the amine.

From which of the two groups the inert substances are chosen depends on the framework production conditions. Without particular requirements on the basis of production circumstances, nitrogen is to be preferred as a rule, because on the basis of its low molecular weight this has significantly greater effects with respect to lowering of the vaporization temperature of the amine than dichlorobenzene, as a result of which the streams of inert substance required can be significantly lower. However, if the other production circumstances impose particular requirements, for example in the working up of gaseous hydrogen chloride formed in the phosgenation, it may also be advantageous to employ inert substances from the group of compounds which are gaseous only above room temperature, for example dichlorobenzene. The hydrogen chloride can be worked up to chlorine, for example, by the Deacon process known from the literature (WO2004 014845), i.e. oxidatively in the presence of a catalyst. If the hydrogen chloride is worked up by the Deacon process to give chlorine, which can be at least partially used again for the preparation of phosgene by reaction of carbon monoxide with chlorine, it may be advantageous, depending on the exact amounts of streams of inert substance, to employ an inert substance which can be condensed, such as dichlorobenzene, since in this case sluicing of nitrogen out of the phosgenation process is dispensed with in the Deacon process. If the gaseous stream of hydrogen chloride from an isocyanate process contains relatively large amounts of nitrogen, as a result the valuable product HCl gas is diluted in the Deacon process, so that the gas load of the apparatuses increases, which leads to higher apparatus costs. Sluicing out of the amounts of nitrogen from a stream of hydrogen chloride in the Deacon process is furthermore associated with a not inconsiderable outlay, and increases operating costs. However, if the amount of inert substance already gaseous at room temperature employed is not too high, if a Deacon process is employed for working up the hydrogen chloride formed it may also be advantageous to employ nitrogen or other inert substances which are gaseous at room temperature. In addition to the problems described above which variations in the inert gas stream have on vaporization of the amine, in the case of the oxidative recovery of hydrogen chloride to give chlorine by the Deacon process which follows the isocyanate production, variations in the inert gas stream furthermore also make working up of the hydrogen chloride in the Deacon process difficult, so that the use of the process according to the invention is very particularly advantageous here.

In a preferred embodiment of the process according to the invention, therefore additionally (iii) the HCl formed in the reaction of phosgene and amine is at least partially converted into chlorine in a Deacon process.

It may be preferable in particular on the one hand to utilize the advantages of the addition of an inert compound to the vaporization of the amine in a gas phase phosgenation, without thereby having the disadvantage of dilution of hydrogen chloride gas, the product coupled with the reaction, in the conversion of the hydrogen chloride gas into chlorine in a Deacon process. In this case, preferably, inert substance is added in an amount such that (iv) the molar ratio of the inert substance introduced into the reactor with the stream containing amine to the HCl fed into the Deacon process is always between>0 and 25 mol %, preferably between>0 and 11 mol %, particularly preferably between 0.025 and 5 mol %.

According to the process according to the invention, the reaction of phosgene with the aromatic amines is carried out in the gas phase. Reaction in the gas phase is to be understood here as meaning that the reaction conditions are chosen such that the educts, reaction intermediate products and products and inert substances metered in remain predominantly in the gas phase during passage through the reaction space during the course of the reaction, in particular to the extent of≥95% by weight, preferably to the extent of≥98% by weight, particularly preferably≥99% by weight, very particularly preferably≥99.8% by weight and specifically to the extent of≥99.9% by weight, in each case based on the weight of the reaction mixture. Intermediate products in this context are, for example, monoamino-monocarbamoyl chlorides, dicarbamoyl chlorides, monoamino-monoisocyanates and monoisocyanato-monocarbamoyl chlorides formed if diamines are employed, and the hydrochlorides of the particular amino compounds.

The reaction according to the invention of phosgene with aromatic amines is carried out in at least one reaction space, which is arranged in a reactor, i.e. reaction space is understood as meaning the space in which the reaction of the educts and intermediate products takes place, and reactor is understood as meaning the technical device which contains the reaction space. A reactor here can also contain several reaction spaces. The educts and the inert substances metered in are in general fed to the reaction space via at least one mixing device. The process according to the invention can in principle be applied to any reaction space and reactor geometry.

In a further preferred embodiment of the process according to the invention, the reactor has, after the reaction space in which, after mixing of the educts, a conversion of the amine groups into the isocyanate groups of 80%, preferably 90%, particularly preferably 99%, very particularly preferably 99.5% is reached, a rotationally symmetric reaction space with a constant and/or widened flowed-through cross-sectional area.

The process according to the invention can in principle be applied to any procedure. The adiabatic procedure described in EP-A-1 935 876 is preferred. However, the process described is also advantageous in an isothermal procedure, since in spite of the isothermal procedure, which can be achieved, for example, by cooling the exothermic reaction externally, because of the speed of the gas phase reaction a very rapid change in the reactor temperature results, which cannot be compensated sufficiently rapidly because of the inertia of the coolant system, so that in the case of an isothermal procedure of the reaction temperature variations also occur in the reactor, with the disadvantages described in the prior art.

Before the phosgenation is carried out, the starting amines are preferably vaporized and are heated to 200° C. to 600° C., preferably 200° C. to 500° C., particularly preferably 250° C. to 450° C., and are fed to the reaction space in a form diluted with at least one inert substance according to the above definition.

Preferably, the inert substance is fed to the vaporization, and particularly preferably the inert substance is fed to the vaporization at the point at which the amine is at least completely or partially converted from the liquid into the gaseous phase. However, it is also conceivable in principle to feed the inert substance into the vaporization downstream of the position of at least partial conversion of the amine from the liquid into the gaseous phase. It is furthermore possible first to mix the amine with the inert substance, to charge it with this or to bubble the inert substance into it in a suitable container and to feed the stream obtained in this way into the vaporization.

Inert substances which are already gaseous at room temperature are preferably fed to the vaporization in gaseous form. Inert substances which are gaseous only above room temperature can be introduced into the amine vaporization in either liquid form or gaseous form, i.e. after prior vaporization. However, it is also possible for the inert substances which are gaseous only above room temperature first optionally to be mixed with the amine in the desired ratio in a suitable container and for the stream obtained in this way to be vaporized together.

If the inert substance fed in is gaseous at room temperature, it is preferably fed to the vaporization with a temperature of from −30° C. to 600° C., preferably 0 to 500° C., particularly preferably 50 to 400° C. Various apparatuses are suitable for achieving this temperature, such as, for example, tube bundle heat exchangers with a coolant or heating agent or electrically operated heaters or other apparatuses. The inert substance fed in which is gaseous at room temperature particularly preferably has a temperature difference from the boiling point of the amine at the given vaporization pressure of not more than 150° C., preferably not more than 100° C.

If the inert substance fed in is gaseous only above room temperature, if it is fed into the reactor in gaseous form it is first vaporized and preferably fed to the amine vaporization with a temperature of from 200° C. to 600° C., particularly preferably with a temperature of from 250° C. to 500° C. The gaseous inert substance fed in which is gaseous only above room temperature particularly preferably has a temperature difference from the boiling point of the amine at the given vaporization pressure of not more than 150° C., preferably not more than 100° C.

All the apparatuses known to the person skilled in the art are suitable for generating a gaseous inert stream of a substance which is gaseous only above room temperature.

If the substance which is gaseous only above room temperature is first mixed with the amine, the temperature of the inert substance can vary widely. A temperature range of from minus 30° C. to 200° C., and preferably 0 to 180° C. is possible. It is also possible for the mixture obtained from the amine and the inert substance which is gaseous only above room temperature to be heated together and to be passed into the vaporization as a mixture. However, it is also possible to heat the two streams separately and to combine them only in the vaporization.

It is also possible in principle to employ mixtures of various inert substances. Mixtures of substances which are already gaseous at room temperature and substances which are gaseous only above room temperature can be advantageous. This can be preferable in particular if on the one hand the advantage of a lowered vaporization temperature is to be combined with a high purity of hydrogen chloride gas, the gaseous coupled product.

A sufficient constant nature according to the invention of the ratio of the streams is preferably achieved by a constant and uniform, preferably uniform over time, mixing of the streams. In particular, a sufficient constant nature of the ratio of the streams is achieved by a procedure in which the smaller of the streams in amount, i.e. the inert substance fed in, is fed in with a constant amount and in a stable manner over time.

Suitable measures by means of which inert compounds which are already gaseous at room temperature can be fed in constantly and in a stable manner over time are known to the person skilled in the art. It may be mentioned here by way of example but not limitation, however, that the gas pressure of the gaseous stream fed in is sufficiently high to render possible a regulated and stable feeding in. The pressure in the feed, i.e. in the feed line directly before entry into the vaporizer, of the inert substance fed in is thus preferably higher than the pressure which prevails in the vaporization apparatus. Particularly preferably, the pressure is at least 10 mbar, very particularly preferably at least 50 mbar, and particularly preferably at least 150 mbar higher than the pressure in the vaporization apparatus. In general, the pressure is not more than 100 mbar higher. Particularly preferably, inert substances fed into the reactor in gaseous form are measured, and stirred into the reactor in a regulated manner. Suitable measuring instruments and regulating instruments are prior art. Other measures are likewise possible.

If a substance which is gaseous only above room temperature is used as the inert substance, and this substance is mixed in the liquid form with the amine before the vaporization, the sufficient constant nature of the ratio of the streams is achieved by mixing liquid streams. For this, the smaller of the streams in amount, i.e. the inert stream, is fed in with a constant amount and in a stable manner over time. Suitable measures for metering liquid streams in a constant manner are known to the person skilled in the art. Suitable metering in a constant amount and in a stable manner over time can be effected, for example, with a metering pump, but filling into a container and mixing, for example by means of a stirrer, is also conceivable. Other measures are likewise possible.

Preferably, these measures ensure that within a period of 20 minutes the molar stream of inert substance or the sum of the molar streams of all the inert substances changes by not more than 99%, preferably not more than 80%, particularly preferably not more than 60%. As a result, marked variations in the ratio of the sum of the molar streams of all the inert-substances to the molar stream of the amine groups are avoided, so that within a period of 20 minutes this ratio changes by not more than 99%, preferably not more than 80%, particularly preferably not more than 60%. The problems described above in connection with disturbances in the inert gas stream are consequently effectively reduced or avoided completely. By adhering to a molar ratio of the inert substance to the amino groups in the stream containing the amine and the inert substance to the reactor of $>0$ and $<45$ mol %, preferably from $>0$ to 25 mol % and particularly preferably from 0.1 to 10 mol %, gentle vaporization of the amine is ensured.

Preferably, it is furthermore ensured by these measures that variations in the composition in the material stream of hydrogen chloride, the gaseous product coupled with the reaction, are avoided. By the composition of the gaseous stream of hydrogen chloride being stabilized over time in this way, disturbances in the Deacon process are avoided.

The vaporization of the starting amines can be carried out in all known vaporization apparatuses. Vaporization systems in which a small work content is led with a high circulating output over a falling film evaporator, wherein to minimize the exposure of the starting amines to heat the vaporization operation is assisted by feeding in at least one inert substance, are preferably employed.

In a particularly preferred embodiment, vaporization systems in which a small work content is circulated over at least one micro-heat exchanger or micro-evaporator are employed. The use of appropriate heat exchangers for vaporization of amines is disclosed e.g. in EP-A-1 754 698. The apparatuses disclosed in paragraphs [0007] to [0008] and [0017] to [0039] of EP-A-1 754 689 are preferably employed in the process according to the invention.

The vaporized mixture of amine and at least one inert substance can also contain contents of non-vaporized droplets of amine, and in the case where those inert substances which are gaseous only above room temperature are used, under certain circumstances also additionally contents of non-vaporized inert substance. The vaporized mixture of amine and inert substance can thus be in the form of an aerosol. Preferably, however, the vaporized mixture of amine and inert substance essentially contains no droplets of non-vaporized amine and/or non-vaporized inert substance, that is to say a maximum of 0.5% by weight, particularly preferably a maximum of 0.05% by weight of the vaporized mixture of amine and inert, substance, based on the total weight of the vaporized mixture of amine and inert substance, is in the form of non-vaporized droplets. The remaining part of the vaporized mixture of amine and inert substance is in vaporous form. Very particularly preferably, the vaporized mixture of amine and at least one inert substance contains no droplets of non-vaporized contents. Preferably, after the vaporization the mixture of amine and at least one inert substance is brought to the desired use temperature via an after-heater.

The vaporization and superheating of the starting amines/inert substances furthermore is preferably carried out in several stages in order to avoid non-vaporized droplets in the gas stream of amine and at least one inert substance. Multi-stage vaporization and superheating steps in which droplet separators are incorporated between the vaporization and superheating systems and/or the vaporization apparatuses also have the function of a droplet separator are preferred in particular. Suitable droplet separators are described e.g. in "Droplet Separation", A. Bürkholz, VCH Verlagsgesellschaft, Weinheim—New York—Basle—Cambridge, 1989. Droplet separators which cause a low pressure loss are particularly preferred. Very particularly preferably, the vaporized mixture of amine and at least one inert substance is brought to the desired use temperature via at least one after-heater, which also functions as a droplet separator. Particularly preferably, this after-heater has a liquid drain in order to ensure constant emptying of the separator. After leaving the last superheater in the direction of flow, the mixture of amine and at least one inert substance which has been preheated to its intended temperature is fed with an average dwell time of from preferably 0.01 to 60 s, very particularly preferably from 0.01 to 30 s, particularly preferably 0.01 to 15 s to the reactor or the mixing device thereof for reaction. The risk of a renewed formation of droplets is counteracted here via technical measures, e.g. an adequate insulation to avoid losses by radiation. The reactor running time is increased significantly by generation of an essentially droplet-free gas stream of amine and at least one inert substance before entry into the reactor.

In a preferred embodiment, feeding of the gas stream of amine and at least one inert substance to the reactor or at least one mixing device thereof takes place with a low pressure loss without a regulating device. However, regulated feeding is likewise possible. A division of the gas stream of amine and at least one inert substance into several part streams, which are then fed as described e.g. in EP-A-1 449 826 in paragraphs [0019] to [0022] to a reaction space or, as described e.g. in WO 2008/055898 p. 8, l. 25 to p. 15, l. 31 and in particular p. 23, l. 19-31, to several mixing devices, is also possible. In the case of a division of the gas stream of amine and at least one inert substance, the feeding of the part streams preferably also takes place with a low pressure loss without additional regulating devices. However, separately regulated feeding of the part streams is also possible.

In the process according to the invention, it is advantageous to employ phosgene in excess with respect to the amine groups to be reacted. Preferably, a molar ratio of phosgene to amine groups of from 1.1:1 to 20:1, preferably 1.2:1 to 5:1 is present. The phosgene is also heated to temperatures of from 200° C., to 600° C. and, optionally likewise diluted with at least one inert substance according to the above definition, is fed to the reaction space.

In a preferred embodiment, regulated feeding of the phosgene stream to the reactor or at least one mixing device thereof takes place. However, feeding with a low pressure loss without a regulating device is likewise possible. A division of the phosgene stream into several part streams, which are then fed as described e.g. in WO 2008/055898 p. 8,1. 25 to p. 15, 1. 31 and in particular p. 23, 1. 19-31 to several mixing devices of a reactor, is also possible. Feeding of the part streams to several reactors is also possible. In the case of a division of the phosgene stream, separately regulated feeding of the phosgene part streams preferably takes place.

The process according to the invention is preferably carried out such that the separately heated reaction partners are introduced via at least one mixing device into at least one reaction space, mixed, and reacted taking account of suitable reaction times under a preferably adiabatic reaction procedure. The isocyanate is then condensed by cooling the gas stream, the cooling taking place down to a temperature above the decomposition temperature of the corresponding carbamic acid chloride, that is to say, for example, toluylenediamine acid chloride in the case of TDA.

The necessary dwell time for reaction of the amine groups with the phosgene to give isocyanate is between 0.05 and 15 seconds, depending on the nature of the amine employed, the start temperature, where appropriate the adiabatic increase in temperature in the reaction space, the molar ratio of amine employed and phosgene, the nature and amount of the at least one inert substance and the reaction pressure chosen.

Reactors with essentially rotationally symmetric reaction spaces in which the gaseous educts and at least one inert substance are fed to the at least one mixing space in accordance with the jet mixer principle (see *Chemie-Ing-Techn.* 44 (1972) p. 1055, FIG. 10) are particularly preferably employed. In this context, the substance streams fed in (i.e. amine and at least one inert substance on the one hand and phosgene, optionally diluted with inert substances, on the other hand) preferably enter into the at least one mixing space of the reactors with a speed ratio of 2-20, particularly preferably 3-15, very particularly preferably 4-12. Preferably, in this context the mixture of amine and at least one inert substance is fed with the higher flow rate to the at least one mixing space of the reactors.

Preferably, neither the reaction space nor any mixing units or mixing spaces have heating surfaces, which could give rise to exposure to heat with the consequence of secondary reactions, such as isocyanurate or carbodiimide formation, or cooling surfaces, which could give rise to condensation with the consequence of deposits. The components are preferably reacted adiabatically in this way, apart from any losses by radiation and conduction. In this context, the adiabatic temperature increase in the mixing unit and reactor or reactor is established solely via the temperatures, compositions and relative meterings of the educt streams and the dwell time in the mixing units and the reactors.

After the phosgenation reaction has taken place in the reaction space, the gaseous reaction mixture, which preferably comprises at least one isocyanate, phosgene, at least one, preferably exactly one, inert substance and hydrogen chloride, is preferably freed from the isocyanate formed. This can be carried out, for example, by subjecting the reaction mixture continuously leaving the reaction space to a condensation in an inert solvent, as has already been recommended for other gas phase phosgenations (EP-A-0 749 958).

Preferably, however, the condensation is carried out by a procedure in which the reaction space employed in the process according to the invention has at least one zone into which one or more suitable streams of liquid ("quench liquids") are sprayed for discontinuation of the reaction of the amines employed and the phosgene to give the corresponding isocyanates. By this means, as described in EP-A-1 403 248, rapid cooling of the gas mixtures can be carried out without the use of cold surfaces.

In a particularly preferred form of the process according to the invention, the at least one zone (cooling zone) is integrated into a quenching stage, such as has been disclosed e.g. in EP-A-1 403 248. In a particularly preferred form, several cooling zones are employed. Integration and operation of these at least two cooling zones are preferably effected with a quenching stage. This is disclosed with respect to construction and operation in EP-A-1 935 875.

Instead of the integrated combination of the at least one cooling zone of a reactor with a quenching stage, such as has been disclosed in EP-A-1 935 875, the corresponding integrated combination of the cooling zones of several reactors with a quenching stage is likewise possible. Preferably, however, the integrated combination of a reactor with at least one cooling zone with a quenching stage is preferred.

In a preferred embodiment of the process according to the invention, the throughput capacity of the reactor employed under the reaction conditions required according to the invention is >1 t of amine/h, preferably 2-50 t of amine/h, particularly preferably 2-12 t of amine/h. These values particularly preferably apply to toluylenediamine, 1,6-diaminohexane and to isophoronediamine. In this context, throughput capacity is to be understood as meaning that the stated throughput capacity of amine per h can be reacted in the reactor.

Regardless of the nature of the cooling chosen, the temperature of the at least one cooling zone is preferably chosen such that on the one hand it is above the decomposition temperature of the carbamoyl chloride corresponding to the isocyanate, and on the other hand the isocyanate and inert substances employed which are gaseous only above room temperature to the greatest extent condense or to the greatest extent dissolve in the solvent. Excess phosgene, hydrogen chloride and inert substances which are gaseous at room temperature are preferably to the greatest extent not condensed or not dissolved in the condensation or quenching stage. Solvents kept at a temperature of from 80 to 200° C., preferably 80 to 180° C., such as, for example, chlorobenzene and/or dichlorobenzene, or isocyanate or mixtures of the isocyanate with chlorobenzene and/or dichlorobenzene kept in this temperature range are particularly suitable for selective isolation of the isocyanate from the gaseous reaction mixture. On the basis of the physical data at a given temperature, pressure and composition, the person skilled in the art can easily predict what weight content of the isocyanate condenses in the quenching or passes through this without being condensed. It is likewise easy to predict what weight content of the excess phosgene, hydrogen chloride and at least one inert substance passes through the quenching without being condensed or dissolves in the quenching liquid.

Generation of the flow, which is preferred for the process according to the invention, of the gaseous reaction mixture as a flow through the reaction space without substantial backmixing is ensured by a pressure gradient over the reaction space. The pressure gradient preferably exists between the educt feed lines before the mixing on the one hand and the exit from the condensation or quenching stage on the other hand. Preferably, the absolute pressure in the educt feed lines before the mixing is 200 to 3,000 mbar and after the condensation or quenching stage is 150 to 2,500 mbar. However, it is essential here merely to maintain a pressure difference from the educt feed lines via the reaction space to after the condensation or quenching stage of preferably at least 50 mbar for the purpose of ensuring the directed flow mentioned and a good mixing of the educts.

The gas mixture leaving the condensation or quenching stage is preferably freed from residual isocyanate in a downstream gas wash with a suitable wash liquid, and is preferably the then freed from excess phosgene in a manner known per se. This can he carried out by means of a cold trap, absorption in an inert solvent (e.g. chlorobenzene or dichlorobenzene) or by adsorption and hydrolysis on active charcoal. The hydrogen chloride gas passing through the phosgene recovery stage can be recycled in a manner known per se for recovery of the chlorine required for the phosgene synthesis. The wash liquid obtained after its use for the gas wash is then preferably at least partially employed as the quench liquid for cooling the gas mixture in the corresponding zone of the reaction space.

The isocyanates are subsequently preferably prepared in a pure form by working up the solutions or mixtures from the condensation or quenching stage by distillation.

EXAMPLES

Example 1

Comparison Example 20.5 kmol/h of a mixture comprising 2.4- and 2,6-toluylenediamine in the weight ratio of 80% to 20% are vaporized together with 17.85 kmol/h of nitrogen at approx. 280° C. and are passed in gaseous form to a rotationally symmetric tube reactor with a downstream isocyanate condensation stage with a temperature above 300° C. At the same time, in parallel with this gaseous phosgene is fed to the tube reactor, likewise with a temperature above 300° C. The streams are injected into the mixing zone through a nozzle and mixed and enter into the reaction space. The reaction in the reaction space takes place adiabatically within a dwell time of less than 10 seconds. The gas mixture is passed through a condensation stage and is thereby cooled to a gas temperature of approx. 165° C. The condensate obtained is fed to a distillation sequence and gives pure TDI. The non-condensed gas mixture is washed with o-dichlorobenzene in a subsequent washing and the by-product HCl is separated from the excess phosgene by absorption.

Within 8 min the amount of nitrogen first falls to approx. 20% of the original value, in order then to rise to approx. 150% of the original value. As a result, the amount of TDA first falls to approx. 40% of the original amount, in order then to rise to approx. 125% of the original amount. As a result, the average dwell time in the reactor varies by more than +– 10%. Inspection of the mixing nozzle shows deposits. The temperature variations measured on the outer wall on the reactor are +– 3° C.

Example 2

According to the Invention 20.5 kmol/h of a mixture comprising 2.4- and 2,6-toluylenediamine in the weight ratio of 80% to 20% are vaporized together with 17.85 kmol/h of nitrogen at approx. 280° C. and are passed in gaseous form to a rotationally symmetric tube reactor with a downstream isocyanate condensation stage with a temperature above 300° C. At the same time, in parallel with this gaseous phosgene is fed to the tube reactor, likewise with a temperature above 300° C. The streams are injected into the mixing zone through a nozzle and mixed and enter into the reaction space. The reaction in the reaction space takes place adiabatically within a dwell time of less than 10 seconds. The gas mixture is passed through a condensation stage and is thereby cooled to a gas temperature of approx. 165° C. The condensate obtained is fed to a distillation sequence and gives pure TDI. The non-condensed gas mixture is washed with o-dichlorobenzene in a subsequent washing and the by-product HCl is separated from the excess phosgene by absorption.

Within 20 min, the amount of nitrogen based on the TDA gas amount changes by not more than plus/minus 5%. The average dwell time in the reactor varies by not more than 6%, no temperature changes are measured on the reactor wall. Inspection of the mixing nozzle shows no deposits.

What is claimed is:

1. A process for the continuous production of an isocyanate comprising
   a) introducing a phosgene-containing stream and a stream comprising an amine and an inert substance into a reactor, and
   b) reacting the amine with phosgene in the presence of the inert substance in the gas phase,
   under conditions such that:
      (i) an inert substance to amine molar ratio of greater than 0 but less than 45 mol % is maintained, and
      (ii) this molar ratio changes by a maximum of 99% in each 20 minute period.

2. The process of claim 1 in which the inert substance is nitrogen and/or one or more noble gases.

3. The process of claim 1 in which the inert substance is chlorobenzene, chlorotoluene, dichlorobenzene, toluene, xylene, chloronaphthalene, dccahydronaphthalenc or a mixture thereof.

4. The process of claim 1 in which hydrogen chloride formed by reacting the amine with the phosgene is at least partially converted to chlorine in a Deacon process.

5. The process of claim 4 in which the inert substance introduced into the reactor with the amine and the amount of hydrogen chloride fed into the Deacon process arc used in amounts such that the molar ratio of the inert substance to the hydrogen chloride is always greater than 0 but less than 25 mol %.

6. The process of claim 1 in which the stream containing the amine and the inert substance is removed from a vaporizer in which the amine is vaporized and into which the inert substance is fed in gaseous form.

7. The process of claim 6 in which the pressure of the inert substance directly before entry into the vaporizer is at least 10 mbar higher than pressure in the vaporizer.

8. The process of claim 1 in which the amine is toluenediamine, diaminohexane or isophoronediamine.

* * * * *